United States Patent [19]
Takemoto

[11] Patent Number: 5,830,855
[45] Date of Patent: Nov. 3, 1998

[54] LIPODEPSIPEPTIDES AS ANTIFUNGAL AND FUNGICIDAL AGENTS

[75] Inventor: Jon Y. Takemoto, North Logan, Utah

[73] Assignee: Utah State University, Logan, Utah

[21] Appl. No.: 713,996

[22] Filed: Sep. 12, 1996

Related U.S. Application Data

[60] Provisional application No. 60/003,604, Sep. 12, 1995.
[51] Int. Cl.$^6$ .............................. A61K 38/12; C07K 5/00; C07K 7/00; C07K 16/00
[52] U.S. Cl. ................................. 514/11; 514/9; 530/317
[58] Field of Search ................................. 530/317; 514/9, 514/11

[56] References Cited

U.S. PATENT DOCUMENTS 5,576,298  11/1996  Strobel et al. .............................. 514/15

OTHER PUBLICATIONS

"Properties of Voltage–Gated Ion Channels Formed by Syringomycin E in Planar Lipid Bilayers", Feigin et al., *The Journal of Membrane Biology,* 1996, pp. 41–47.

"Bacterial Phytotoxin Syringomycin and its Interactions with Host Membranes", Takemoto, *Molecular Signals in Plant–Microbe Communications,* 1991, pp. 247–260.

Harrison, et al, J. Gen Microbiology., (1991) vol. 137, 12, (2857–2865).

Sorensen et al Antimicrobial Agents and Chemothearpy 40(12) 2710–2713, 1996.

Grgurina et al, Experientia 50/2; pp. 130–133, 1994.

*Primary Examiner*—Cecilia J. Tsang
*Assistant Examiner*—S. G. Marshall
*Attorney, Agent, or Firm*—Madson & Metcalf

[57] ABSTRACT

Lipodepsipeptides from *Pseudomonas syringae* pv. *syringae* were evaluated for antifungal activity. Specifically, the in vitro antifungal and fungicidal activities of three cyclic lipodepsinonapeptides syringomycin E, syringotoxin B, and syringostatin A against medically important isolates were evaluated using a standard broth microdilution susceptibility method. Erythrocyte toxicity was also evaluated. All three compounds showed broad antifungal activity and fungicidal action against most of the fungi tested.

In addition, the present invention relates to a novel method for suppressing the immune system of mammals using cyclic lipodepsipeptides. The ability of cyclic lipodepsipeptides to suppress the immune system was evaluated in mitogen-induced lymphocytes. One cyclic lipodepsipeptide, syringomycin-E significantly inhibited mitogen--induced lymphocytes stimulation by pokeweed mitogen, phytohemagglutinin, and monoclonal antibodies to CD3. These results indicate that lipodepsipeptides are useful at suppressing both cellular and humoral immune responses.

11 Claims, 4 Drawing Sheets

LIPODEPSIPEPTIDES AS ANTIFUNGAL AND FUNGICIDAL AGENTS

RELATED APPLICATIONS

This application is related to United States Provisional patent application Ser. No. 60/003,604, filed Sep. 12, 1995.

1. The Field of the Invention

The present invention is related to peptides from the plant bacterium *Pseudomonas syringae* pv. *syringae* with antifungal and immunosuppressive activity. More specifically, the present invention relates to the use of lipodepsipeptides, and derivative of lipodepsipeptides, as antifungal and immunosuppressive agents.

2. Technical Background

Fungi are eukaryotic organisms which are wide spread in nature and grow well in a broad range of environmental conditions. The term fungi generally includes mushrooms, puffballs, woody bracket fungi, molds and yeast. Thus, fungi may be single-celled or multicellular organisms.

Fungi are heterotrophic because they do not contain chlorophyl. Fungi depend on organic products as a source of energy. Many fungi actively produce enzymes which enable them to break down complex substances for energy. Production of these enzymes has numerous beneficial effects, including recycling products in the soil thus enabling some plants to obtain minerals. Furthermore, fungi play a critical role in the processing of many foods, including leavening bread and fermenting beer, wine and cheeses. In addition, they produce antibiotics, such as penicillin, and are a valuable food source, as in the case of mushrooms.

These enzymes, however, can also have undesirable effects on plants and animals, including human. Each year, millions of dollars worth of fruit and vegetables are lost due to fungal damage. Fungi such as *Byssochlamys fulva, Aspergillus* ssp., *Mucor* ssp., and *Saccharomyces cerevisiae* are responsible for spoiling canned foods, fresh fruits and jams, breads, fish, and meats. Traditionally, chemical additives such as sorbic acid and sodium propionate have been used to control fugal growth on food products or to control contamination of equipment used to handle food products.

Other types of fungi produce poisons known as mycotoxins which are very toxic to many animal species and historically have had devastating effects on fish, birds and humans. Most fungal infections, are not life-threatening. Recently, however, fungal infections once dismissed as a nuisance have become a major health concern. Opportunistic fungal infections are increasingly important causes of morbidity and mortality in hospitalized patients. This is especially true for patients with AIDS and other immunocompromised conditions, those receiving broad-spectrum antibiotics, cytotoxic therapy, immunosuppressants or chemotherapy, and patients with intravascular catheters.

Efforts to combat these infections are hampered by lack of fungal specific drugs, increasing drug resistance, and a growing list of pathogens. Because both fungi and higher organisms are eukaryotic, and thus share many biological processes, developing drugs that are specific to fungi has been extremely difficult. The most important antifungal agents are the polyenes such as amphotericin B (AmB), imidazoles such as triazoles, and RNA and DNA inhibitors such as flucytosine.

These agents have several shortcomings. Most notably, fungi have developed resistance against many polyenes, imidazoles and RNA and DNA inhibitors. Moreover, these agents produce numerous side effects. Amphotericin B when used to treat systemic Candidiasis, for example, may cause kidney damage, convulsions, hypotension, nausea, vomiting, abdominal pain, cardiac arrest and anemia. Accordingly, increases in the incidence of fungal infections have prompted a search for new antifungal agents with broad antifungal and, fungicidal activity, and minimal plant and animal toxicity.

At the same time, there is a need in the art for immunosuppressants. Immunosuppressants are particularly important in tissue and organ grafts, cross-species transplantations, blood transfusions, and bone marrow transplants. One area of particular concern is donors and recipients with different histocompatibility. When the donor's mature immunocompetent T cells are transfused, the allogeneic recipient is unable to identify and reject the donor's T cells. As a result, the donor's T cells react against the tissues of the host in a graft-versus-host response. This response triggers many reactions in the host, including skin, gut and liver damage which often leads to death. Therefore, it is critical to the art of organ and tissue transplantation to have effective immunosuppressant agents, which reduce organ and tissue rejection.

Traditionally, X-rays were used to suppress the immune response to foreign organs and tissues. Currently, there are several immunosuppressive drugs available. These include, for example, cyclosporin A , FK506, and rapamycin. Structures and a brief description of the agents are described in Kunz, et al. "Cyclosporin A, FK506, and rapamycin: more than just immunosuppression" which is hereby incorporated by reference. Advantageously, cyclosporin A, FK506, and rapamycin are also antifungal agents. Thus, these drugs simultaneously combat opportunistic fungal infection while the host's immune system is being suppressed.

One concern in the art is that cyclosporin A, FK506, and rapamycin all are structurally and chemically related. It is possible, therefore, that a given host or fungi could become resistant to the immunosuppressive effects or antifungal activity of these agents. Given the rapid development of organ and tissue transplants and the risk for opportunistic mycosis infection, it would be advantageous to the art to have immunosuppressants that are chemically and structurally distinct, and hence are more likely to be effective against opportunistic fungi that are resistant to current immunosuppressants.

From the foregoing, it will be appreciated that it would be an advancement in the art to provide methods for combating cutaneous and invasive fungal infections in mammals. It would be a further advancement in the art if the methods were effective against a broad range of fungi, including those pathogenic to humans. It would be yet another advancement in the art to provide methods for preserving food, and protecting crops and vegetation from fungal pathogens. It would also be an advancement in the art to provide methods for suppressing the immune system of mammals. Finally, it would be an advancement in the art if the immunosuppressive agent was also an antifungal and fungicidal agent and thus could simultaneously combat opportunistic infections during the time when the immune system is suppressed.

Such methods are disclosed and claimed herein.

3. BRIEF SUMMARY OF THE INVENTION

The medical profession is currently facing a growing epidemic of opportunistic fungal infection, particularly among persons with immunocompromised conditions, those receiving broad-spectrum antibiotics, cytotoxic therapy, or chemotherapy and patients with intravascular catheters. Fungi are often classified into subgroups based on their method of reproduction, mycelial formation, cellular structure and formation, and biochemical and physical properties. The term fungi as used herein encompasses all forms of fungi including mushrooms, puffballs, woody bracket fungi, molds and yeast. Many fungi are becoming resistant to conventional antifungal and fungicidal agents. Therefore, there is a critical need in the art for new antifungal and fungicidal agents that to combat mycoses infections.

A class of molecules referred to as cyclic lipodepsipeptides (CLPs) possess antifungal and fungicidal activity. CLPs are naturally produced by certain bacteria such as *Pseudomonas syringae*. While the activity of CLPs has been known for over a decade, scientists in the field believed the bacteria that produced these toxins were pathovars (pathogenic to plants) and that CLPs were phytotoxins (toxic to plants). As a result, the use of CLPs as antifungal and fungicidal agents in plants and animals was not contemplated by scientist in the field. Like other bacterial endotoxins and exotoxins which cause diphtheria, botulism and cholera, CLPs were thought to be highly toxic and therefore useless as antifungal or fungicidal agents. Moreover, the mechanism of action of CLPs is similar to amphotericin B. Both compounds disrupt the permeability of cell membranes. Given the similarity in the two compounds' mechanisms of action, CLPs were not expected to be useful against fungi that had become resistant to amphotericin B and other agents which similarly disrupt fungi membrane.

It has been discovered that CLP are not phytotoxins as once believed. In fact, CLP producing bacteria protect plants from fungal infection and disease. Furthermore, in spite of the similarities between the biochemistry of CLPs and current antifungal and fungicidal agents, CLPs are effective against fungal strains which are resistant to current agents such as amphotericin B. Accordingly, the present invention is directed to a novel method for treating cutaneous and invasive fungal disease in mammals using CLPs. In addition, because CLPs are not phytotoxins, CLPs may be used to preserve food and protect crops and vegetation from fungal pathogens.

In one embodiment, three CLPs were tested for antifungal and fungicidal activity. Syringomycin-E (SR-E), syringostatin-B (ST-B), and syringostatin-A (S S-A ) from *Pseudomonas syringae* pv. *syringae* all displayed fungicidal activities. There was some variability in susceptibility between fungal species. All three CLPs were more active against yeasts than against filamentous fungi. This difference could be due to differences in membrane sterol and phospholipid composition of yeasts and filamentous fungi. Sterols and phospholipids are important for SR-E action. Although inhibited by all three CLPs, *C. neoformans* was particularly sensitive to ST-B.

Besides their antifungal properties, like other antifungal agents, CLPs were lytic to erythrocytes. The lytic activity profile of the three CLPs paralleled their antifungal activities. SR-E and SS-A were more active than ST-B. Conceivably, the more positive net charge of SR-E and SS-A imparted by three basic amino acids verses two of ST-B could account for this difference and also ST-B's higher fungicidal activity against *C. neoformans*.

A significant finding was that AmB-resistant *C. rugosa* was sensitive to CLPs. This is likely due to differences in mechanism of action between AmB and CLPs though, as discussed above, both agents bind membrane sterols and perturb membrane function. Chemical differences between the two classes of compounds probably account for their distinctive actions on membranes. For example, CLPs are water-soluble whereas AmB, a cyclic polyene, is significantly hydrophobic. In short, *P. syringae* pv. *syringae* CLPs are effective antifungal and fungicidal agents. They are fungicidal against important human pathogenic yeasts, water-soluble, and have unique mechanisms of action.

In addition, CLPs also possess significant immunosuppressive properties. In one embodiment, the ability of syringomycin-E to inhibit mitogen-induced lymphocyte proliferation was tested. Based on $[^3H]$-thymidine incorporation, SR-E had no effect on cell proliferation in the absence of mitogens. However, lymphocyte proliferation induced by pokeweed mitogen (PWM), phytohemagglutinin (PHA) and monoclonal antibody to CD3 (anti-CD3) was significantly suppressed in the presence of SR-E. SR-E's suppressive effect was more pronounced with PWM as compared with PHA or anti-CD3.

These and other objects and advantages of the present invention will become apparent upon reference to the accompanying drawings and graphs and upon reading the following detailed description and appended claims.

4. SUMMARY OF THE DRAWINGS

A more particular description of the invention briefly described above will be rendered by reference to the appended drawings and graphs. These drawings and graphs only provide information concerning typical embodiments of the invention and are not to be considered limiting of its scope.

Figure 4:
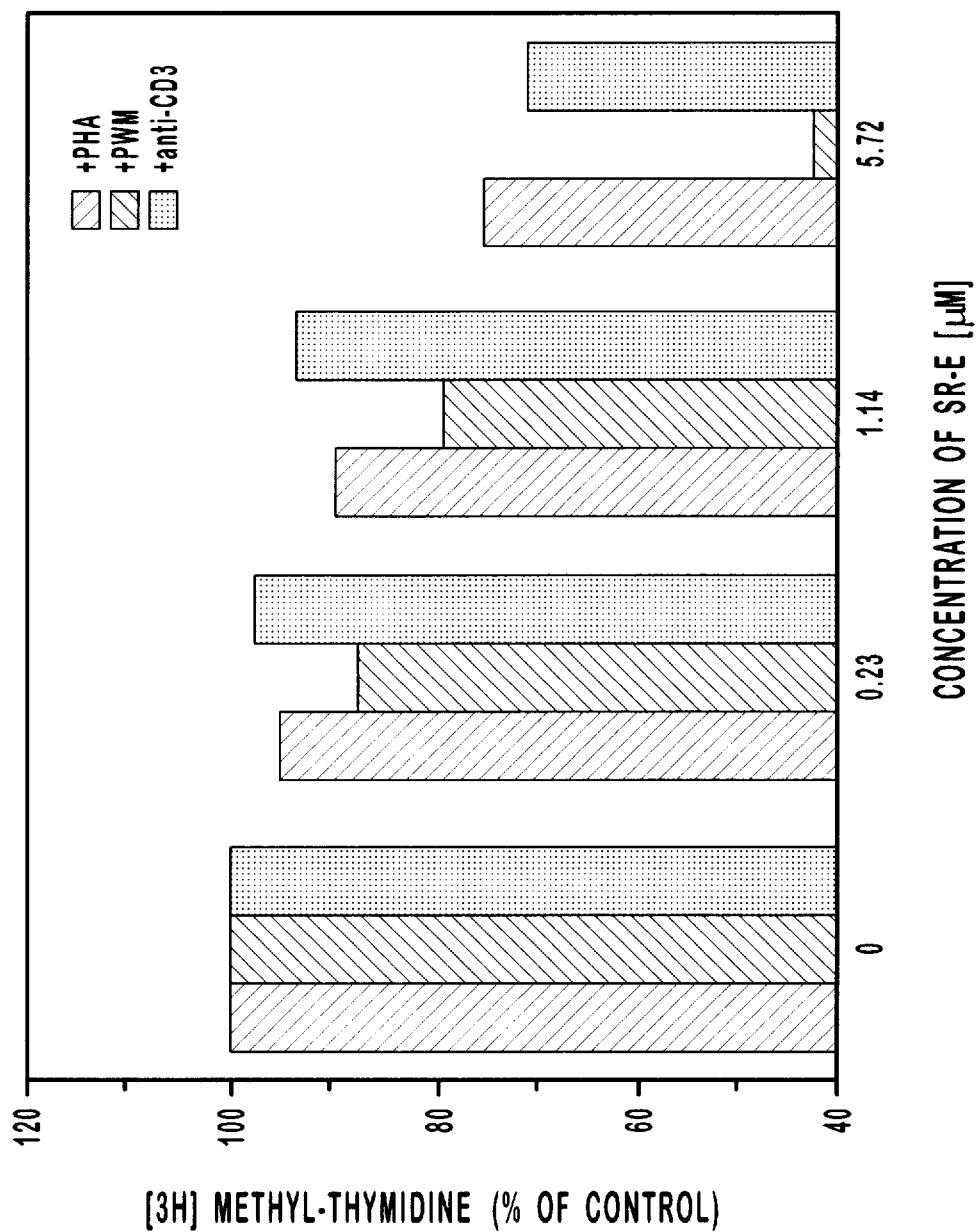

FIG. 4 is a graph illustrating the effect of SR-E on mitogen-activated lymphocyte proliferation. Lymphocytes were cultured in the presence of mitogens PHA (10 μg/well), PWM (20 μg/well) or anti-CD3 (0.4 μg/well). The data represent the mean of three experiments each with triplicate assays.

5. DETAILED DESCRIPTION OF THE INVENTION

The present invention is directed to a novel method of combating human and plant fungal pathogens using lipodepsipeptides. In addition, the present invention is directed to a novel method of suppressing the immune system in mammals using lipodepsipeptides. To better understand the details of the present invention, this section is divided into five sub-sections: structure of lipodepsipeptides, antifungal activity of lipodepsipeptides, fungicidal activity of lipodepsipeptides, erythrocyte toxicity of lipodepsipeptides, and immunosuppressive activity.

5.1. Structure of Lipodepsipeptides

CLPs are composed of a peptide moiety and a hydroxylated acyl chain. The core structure of some lipodepsipeptides is shown below:

acyl chain. However, CLPs may have multiple hydroxyl groups without losing antifungal and fungicidal activity. For example, in the core structure of syringostatin above, syringostatin A has a hydrogen at the R position and syringostatin B as a hydroxyl group at the R position.

5.2 Antifungal Activity of Lipodepsipeptides

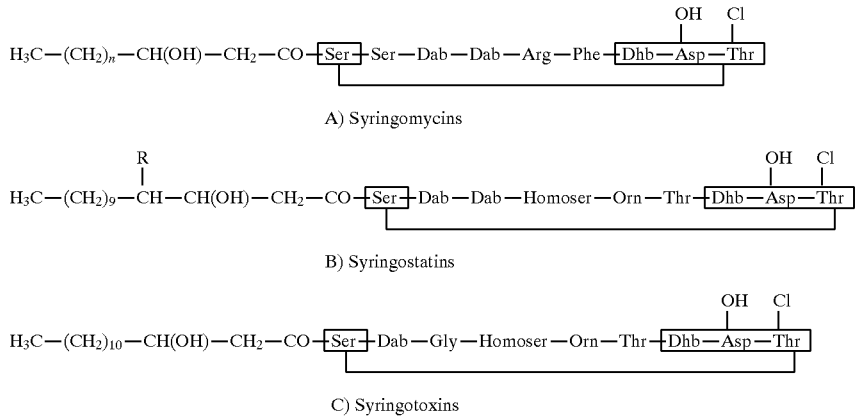

As illustrated above, the peptide is generally nine amino acids and modified amino acids in length. Natural occurring CLPs with less than nine amino acids, such as syringopeptins have been reported and also possess antifungal and fungicidal activity. The peptide is comprised of four amino acids which are conserved between CLPs. These are the N-terminal serine and the C-terminal 2,3-dehydroaminobutryl (Dhb)-3-hydroxyl aspartyl (Asp(3-OH))-4-chlorothreonyl (Thr(4-Cl)) residues (shaded above). The five amino acids between the N-terminal Ser and the C-terminal tripeptide form the variable region of the peptide moiety. As illustrated by the chemical structures above, these amino acids and modified amino acids may be varied significantly without altering the CLPs antifungal and fungicidal activity. The carboxyl of the clorothreonine is covalently bonded to the hydroxyl group of the N-terminal serine to form a macrocyclic ring.

The N-terminal serine is N-acylated by a long-chain unbranched acyl chain. The acyl chain is O-acylated by the C-terminal carboxyl of the acyl chain to form a macrolactone ring. It will be appreciated by one skilled in the art that the length of the acyl chain can vary without significantly altering the CLPs antifungal and fungicidal activity. For example, in the core structure of syringomycin above, syringomycin-$A_1$, syringomycin-E and syringomycin-G have n values of 6, 8 and 10, respectively.

The acyl chain is also hydroxylated. In syringomycin and syringotoxin, the hydroxy group is at the C-3 position of the In one embodiment, three CLPs were tested for antifungal activity. The CLPs showed a broad range of antifungal activity against the fungal isolates (Table 1). SR-E and SS-A had similar activity profiles (except against *Microsporum* spp.) and were overall more active than ST-B. One strain of *C. neoformans* did not follow this pattern and was more susceptible to ST-B than either SR-E or SS-A. This strain was very sensitive to ST-B (0.8 g/ml) and somewhat resistant to AmB (1.25 g/ml). This differential sensitivity to ST-B also occurred with *C. tropicalis* and *C. rugosa*. One strain of *C. tropicalis* and one strain of *C. rugosa* showed resistance to AmB, but were still sensitive to the CLPs. SR-E, SS-A, and ST-B were more active against yeasts (MICs ranging from 0.8 to 25 g/ml) and were least active against the filamentous fungi, *A. fumigatus* (5–40 g/ml) and *Mucor* spp. (6.25–100 g/ml). In addition, ST-B was not as active against the dermatophytes, *Microsporum* spp. and *Trichophyton* spp. (25–200 g/ml). The control organism, *S. cerevisiae* ATCC 36375, gave expected MIC values for AmB and ketoconazole. AmB and ketoconazole, which were used as test standards, had MICs that were within, or close to, the range of the expected values for the clinical isolates (20, 25). These clinical isolates showed a wide range of susceptibility to AmB (0.02–1.25 g/ml) and ketoconazole (0.02–>10 g/ml). MICs for AmB and ketoconazole were generally lower than for the CLPs. One strain of *C. albicans* showed resistance (MIC=10) to ketoconazole, but was sensitive to the other compounds.

TABLE 1

| ORGANISM | No. of Isolates | MFC (μg/ml) range | | | | |
|---|---|---|---|---|---|---|
| | | SR-E | ST-B | SS-A | AmB | Ktz |
| *Candida albicans* | (20) | 2.5–5 | 3.2–12.5 | 2.5–5 | 0.04–0.3 | 0.02–10 |
| *Candida kefyr* | (1) | 2.5 | 3.2 | 2.5 | 0.3 | 0.02 |
| *Candida krusei* | (2) | 10 | 12.5–25 | 10 | 0.3–0.6 | 0.15 |
| *Candida lusitaniae* | (2) | 2.5 | 6.25 | 5 | 0.3 | 0.02 |
| *Candida parapsilosis* | (2) | 2.5 | 6.25–12.5 | 2.5–5 | 0.6 | 0.02 |
| *Candida rugosa* | (2) | 5–20 | 3.2–25 | 10–20 | 0.3–1.25 | 0.02 |

TABLE 1-continued

| ORGANISM | No. of Isolates | MFC (µg/ml) range | | | | |
|---|---|---|---|---|---|---|
| | | SR-E | ST-B | SS-A | AmB | Ktz |
| Candida tropicalis | (2) | 2.5–5 | 3.2 | 2.5–5 | 0.3–1.25 | 0.08–0.6 |
| Cryptococcus neoformans | (14) | 2.5–10 | 0.8–6.25 | 2.5–10 | 0.08–1.25 | 0.04–0.6 |
| Saccharomyces cerevisiae | (1)[a] | 2.5 | 6.25 | 2.5 | 0.3 | 0.15 |
| Aspergillus fumigatus | (16) | 10–20 | 6.25–25 | 5–40 | 0.15–1.25 | 0.3–>10 |
| Mucor spp. | (5) | 10–>40 | 6.25–100 | 10–>40 | 0.02–0.15 | 0.6–>10 |
| Microsporum spp. | (2) | 6.25–12.5 | 25–200 | 2.5–5 | 0.04–0.3 | 0.8–1.6 |
| Trichophyton spp. | (3) | 3.1–6.25 | 25–200 | 2.5–5 | 0.3–0.6 | 0.4–3.1 |

[a]Strain was tested more than once on different days.

5.3 Fungicidal Activity of Lipodepsipeptides

In one embodiment, three CLPs were tested for fungicidal activity. All three CLPs showed fungicidal activity against most of the organisms tested (Table 2). The MFC values were within two-fold dilutions of the respective MICs, except *Mucor* spp. AmB, which is known for its fungicidal action, also showed fungicidal activity against most of the strains tested. Ketoconazole, which is not considered fungicidal, showed fungicidal activity only against *C. krusei*.

TABLE 2

| ORGANISM | No. of Isolates | MFC (µg/ml) range | | | | |
|---|---|---|---|---|---|---|
| | | SR-E | ST-B | SS-A | AmB | Ktz |
| Candida albicans | (20) | 2.5–5 | 3.2–12.5 | 2.5–10 | 015–0.3 | 0.3–>10 |
| Candida kefyr | (1) | 2.5 | 3.2 | 2.5 | 0.3 | 1.25 |
| Candida krusei | (2) | 10 | 12.5–50 | 10–20 | 0.6 | 0.15 |
| Candida lusitaniae | (2) | 2.5–5 | 6.25–12.5 | 5 | 0.6 | ≦0.02 |
| Candida parapsilosis | (2) | 2.5 | 12.5–25 | 2.5–10 | 1.25 | 0.04 |
| Candida rugosa | (2) | 10–20 | 6.25–50 | 10–>20 | 0.6–2.5 | ≦0.02–0.08 |
| Candida tropicalis | (2) | 5 | 12.5 | 5 | 0.6–1.25 | 2.5–10 |
| Cryptococcus neoformans | (14) | 2.5–10 | 0.8–12.5 | 2.5–10 | 0.15–1.25 | 0.08–>10 |
| Saccharomyces cerevisiae | (1)[a] | 2.5 | 12.5–25 | 5 | 1.25 | 0.6–1.25 |
| Aspergillus fumigatus | (16) | 10–>20 | 12.5–>50 | 5–40 | 0.6–2.5 | 2.5–>10 |
| Mucor spp. | (5) | 20–>40 | 25–>100 | 40–>40 | ≦0.02–0.3 | 2.5–>10 |
| Microsporum spp. | (2) | 6.25–12.5 | 25–200 | 5 | 0.08–0.3 | 25–>25 |
| Trichophyton spp. | (3) | 6.25–25 | 25–200 | 5 | 0.3–0.6 | 12.5–>25 |

[a]Strain was tested more than once on different days.

5.4 Erythrocyte Toxicity of Lipodepsipeptides

Figure 1:
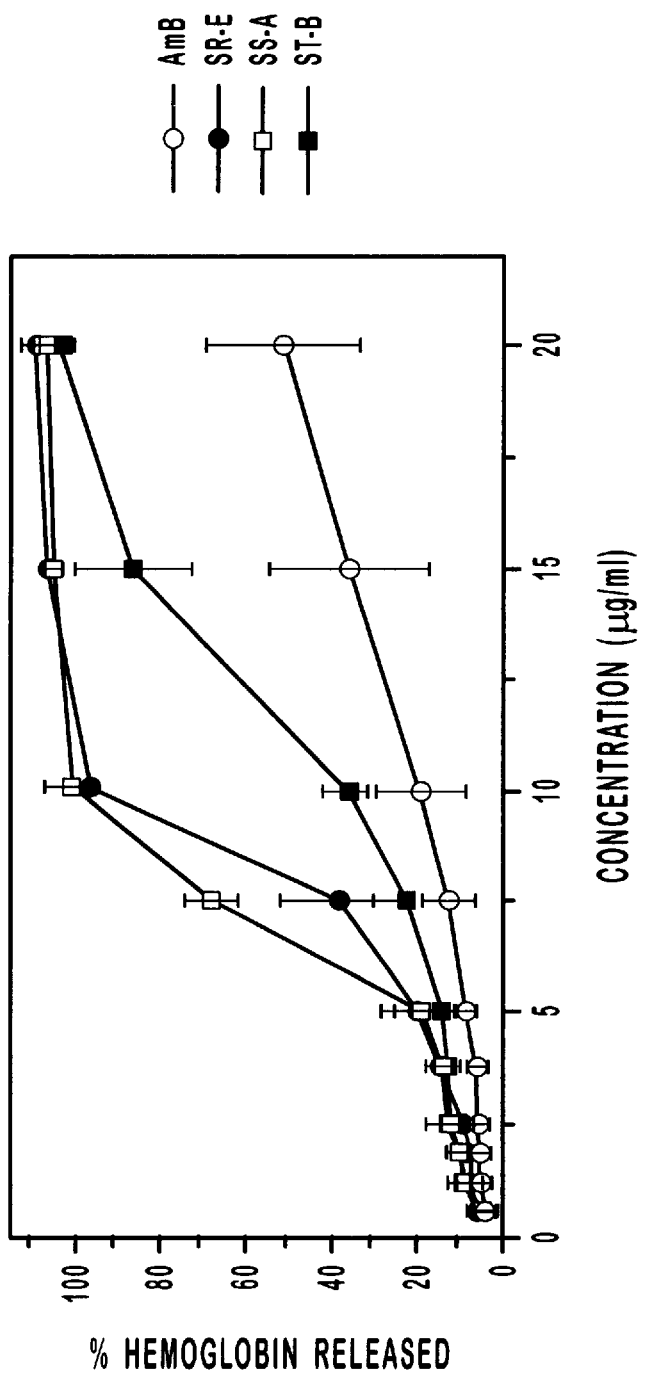
FIG. 1 is a graph illustrating the erythrocyte toxicity of AmB, SR-E, SS-A, or ST-B as measured by hemoglobin release. Sheep erythrocytes were used and were from a single lot and each point represents the mean of three experiments.
Figure 2:
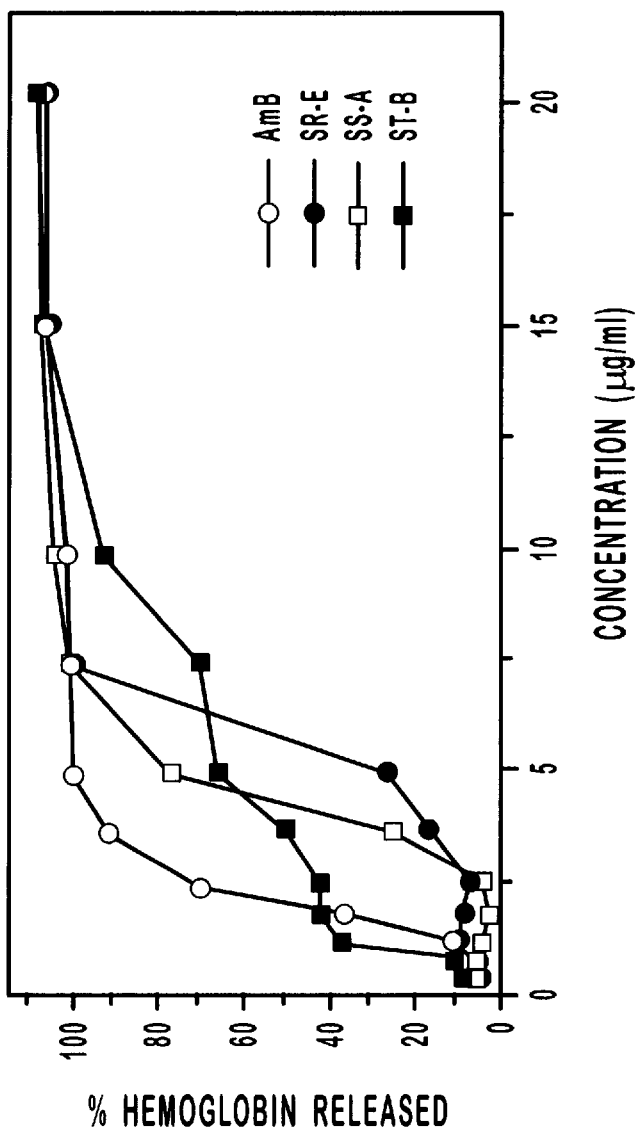
FIG. 2 is a graph illustrating the erythrocyte toxicity of AmB, SR-E, SS-A, or ST-B as measured by hemoglobin release. Sheep erythrocytes were used and were from different lots and each point represents the mean of three experiments.

In one embodiment, the erythrocyte toxicity of three CLPs was tested. As illustrated in FIG. 1, all three CLPs caused lysis of the erythrocytes and in most cases were more toxic to the erythrocytes than AmB. However, as illustrated in FIG. 2, the relative toxicity varied with different lots of erythrocytes. In all studies, ST-B was the least toxic of the three CLPs. The kinetics of hemolysis differed between the CLPs and AmB.

5.5 Immunosuppressive Activity

It is well known in the art that lymphocyte stimulation with mitogens is a measure of cell-mediated immunity, and that it can be used to assess the subset of lymphocytes affected. Inhibition of PHA- and anti-CD3-induced lymphocyte proliferation suggests suppression of cellular immunity (T cell function). Both PHA and anti-CD3 are well known activators of T lymphocytes, although through different mechanisms. Anti-CD3 activates T cells via the T cell antigen receptor (TCR/CD3) complex whereas PHA induces the interleukin-2 (IL-2)/IL-2 receptor (IL-2R) complex. In addition, because PWM is a polyclonal activator of T cell-dependent antibody production by B cells, inhibition of PWM-induced proliferation implies suppression of humoral immunity (B cell function). Accordingly, in one embodiment the ability of SR-E to suppress PHA, PWM and anti-CD3-induced lymphocyte proliferation was tested.

Figure 3:
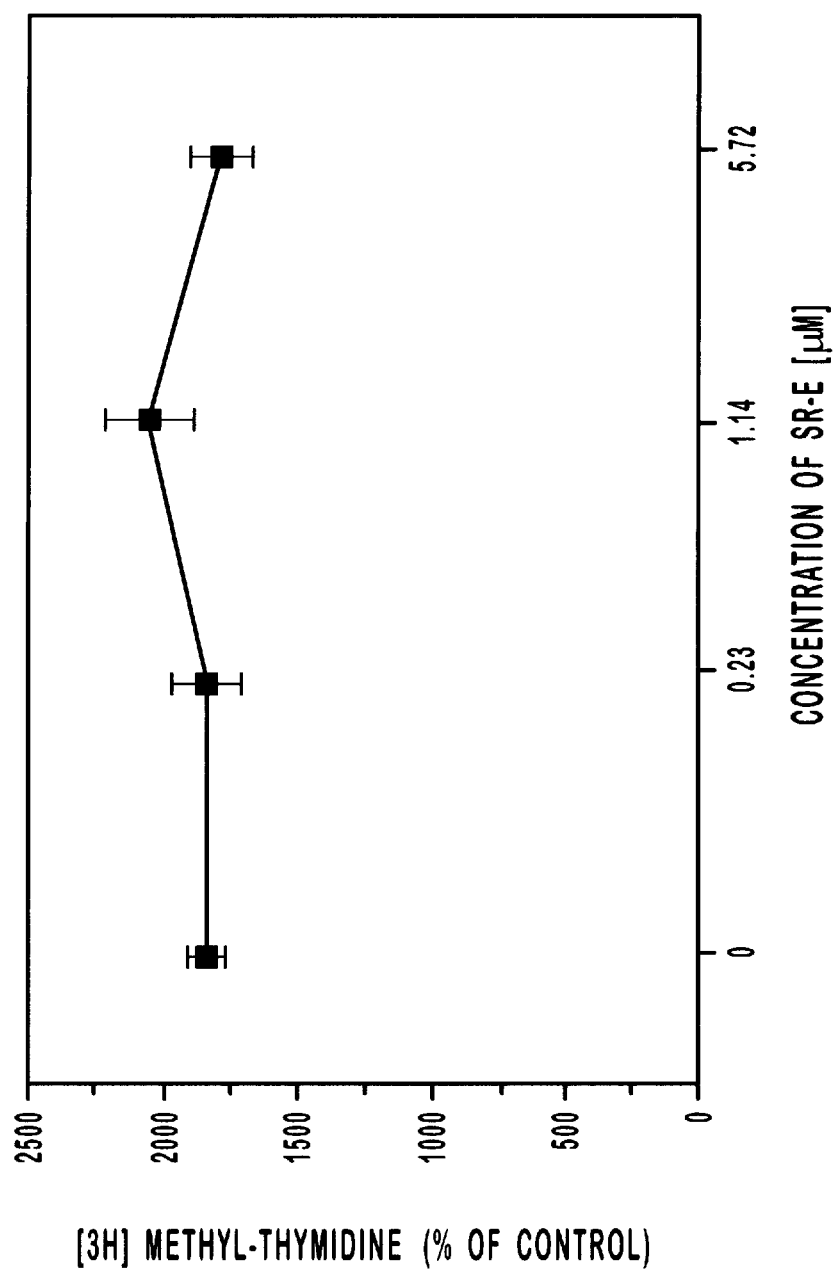
FIG. 3 is a graph illustrating the effect of syringomycin-E on lymphocyte proliferation in the absence of mitogens. The data represent the mean of two different experiments each with triplicate assays.

As expected, PHA, PWM and anti-CD3 each stimulated lymphocyte proliferation several fold above the baseline control (no mitogen). As illustrated in FIG. 3, SR-E at concentrations of 5.72 µM and lower had no effect in the absence of mitogens based on [$^3$H]-thymidine incorporation. However, as illustrated in FIG. 4, mitogen-activated proliferation was suppressed by SR-E at various concentrations. SR-E's degree of inhibition varied according to the mitogen used to induce proliferation. For example, the PWM response was inhibited to a greater degree than the PHA and anti-CD3 responses. At a concentration of 5.72 µM, SR-E suppressed PWM response by 60% (p=0.017), PHA response by 25% (p=0.026) and anti-CD3 response by 30% (p=0.02). Moreover, SR-E at a concentration of 1.14 µM significantly inhibited the PWM response but not PHA and anti-CD3 responses.

6. EXAMPLES

The following examples are given to illustrate various embodiments which have been made with the present invention. It is to be understood that the following examples are not comprehensive or exhaustive of the many types of embodiments which can be prepared in accordance with the present invention.

Example 1

Lipodepsipeptides for Antifungal Experiments: SR-E, ST-B, and SS-A were produced from cultures of *Pseudomo-*

*nas syringae* pv. *syringae* strains B301D, PS268, and SY12, respectively. Strains B301D and PS268 were grown in potato dextrose broth as described by Zhang, L., and J. Y. Takemoto. 1987. Effects of *Pseudomonas syringae* phytotoxin, syringomycin, on plasma membrane functions of *Rhodotorula pilimanae.* Phytopathol. 77(2):297–303. Strain SY12 was grown in syringomycin minimal medium supplemented with 100M arbutin (Sigma Chemical Co., A 4256; St. Louis, Mo.) and 0.1% fructose (SRMAF) (19, 23). SR-E, ST-B, and SS-A were purified by high performance liquid chromatography as described previously by Bidwai, A. P., and J. Y. Takemoto. 1987. Bacterial phytotoxin, syringomycin, induces a protein kinase-mediated phosphorylation of red beet plasma membrane polypeptides. *Proc. Natl. Acad. Sci.* USA. 84:6755–6759. Solubilized AmB containing 35% sodium deoxycholate (Sigma Chemical Co., A 9528; St. Louis, Mo.) and ketoconazole (Sigma Chemical Co., K-1003; St. Louis, Mo.) were used as test standards.

Most of the fungal strains used in the tests were clinical isolates obtained from the University of Texas Health Science Center at San Antonio Fungus Testing Laboratory (San Antonio, Tex.) and the remaining isolates were ATCC strains.

Example 2

Medium: Liquid RPMI 1640 (RPMI) medium with L-glutamine and without sodium bicarbonate (Sigma Chemical Co., R-6504; St. Louis, Mo.) buffered with 0.165M MOPS (34.54 g/liter) was used for in vitro antifungal tests. The medium was adjusted to pH 7.0 with 10M NaOH and filter sterilized.

Example 3

Lipodepsipeptide Dilutions: All stock drug solution concentrations were at least 10-fold higher than the highest concentration tested. AmB, ketoconazole, and the test compounds (SR-E, ST-B, and SS-A) were dissolved in sterile distilled water, 0.2N HCl, and 0.001N HCl, respectively. Each stock solution was diluted to 2× the highest concentration of drug tested with RPMI. Two-fold dilutions were made with RPMI medium.

Example 4

Preparation of Inoculum Suspensions: On Sabouraud dextose agar (SDA; BBL, Becton and Dickinson and Co., Cockeysville, Md.) all isolates were subcultured at least twice before use to ensure purity and viability. *Candida* spp. and *Saccharomyces cerevisiae* were grown for 24 hr at 35° C. Isolates of *Cryptococcus neoformans* were grown for 48 hr at 35° C. Yeast cells from at least five 1-mm-diameter colonies were suspended in 5 ml of sterile 0.85% saline. The resulting suspension was vortexed for 15 sec. The turbidity of each mixed suspension was measured at 530 nm and adjusted to $1\times10^6$ to $5\times10^6$ CFU/ml by the NCCLS spectrophotometric method described by National Committee for Clinical Laboratory Standards. 1992. Reference method for broth dilution antifungal susceptibility testing of yeasts; proposed standard, NCCLS document M27-P (ISBN 1-56238-186-5). NCCLS, Villanova. The final transmission of each yeast suspension ranged from 85–87%.

*Aspergillus fumigatus* and *Mucor* spp. were grown for 1 wk at 35° C. The dermatophytes, *Microsporum* spp. and *Trichophyton* spp., were grown for two wk at 30° C. Fungal spores were washed from the plates of all good spore formers (*A. fumigatus, Mucor* spp., *Microsporum canis* and *Trichophyton* spp.) by placing 5 ml of 0.85% saline with 0.2% Tween 80 on the plates and mixing with an inoculating loop. The spore/mycelium suspension was drawn off with a pipette and allowed to settle for at least 5 min. For the poor spore-forming *Microsporum audouinii,* the procedure was the same except the spore/mycelial suspension was homogenized with a ground glass tissue homogenizer and then allowed to settle for at least 5 min. A small amount of the supernatant was transferred to 5 ml of sterile saline and vortexed. The stock suspensions of all filamentous fungi were measured at 530 nm and adjusted to 85–87% transmission. The concentration ($1\times10^6$ to $5\times10^6$ CFU/ml) was determined by hemacytometer count or plate count on SDA. All stock suspensions were diluted 1000-fold with RPMI, or 2× the final desired test inocula. The 2× inoculum was diluted 1:1 when the wells were inoculated, and the desired inoculum size was achieved.

Example 5

Broth Microdilution Test: Broth microdilution tests were performed using sterile, disposable, multiwell microdilution plates (96 round U-bottom wells) (Falcon 3077; Becton and Dickinson Labware, Lincoln Park, N.J.). The drugs (2× concentrations) were dispensed into the wells of rows number 1 to 10 of the microdilution plates in 100 $\mu$l volumes from highest drug concentration to lowest drug concentration. Each well was inoculated with 100 $\mu$l of the corresponding 2× concentrated fungal suspension. The wells of row 11 contained the inoculum with drug-free media as a positive growth control and the wells of row 12 contained uninoculated-drug-free medium as a sterility control.

Example 6

Incubation and Scoring of MIC: All cultures were incubated without shaking at the temperature used during subculture. Incubation times were 48 hr for *Candida* spp., *S. cerevisiae, A. fumigatus,* and *Mucor* spp; 72 hr for *C. neoformans;* and 7 days for *Microsporum* and *Trichophyton* spp. The microdilution wells were scored from 0, no growth; 1, slightly hazy; 2, prominent decrease in turbidity; 3, slight reduction in turbidity; and 4, no reduction in turbidity when compared to the growth control (drug-free) well. The MICs for SR-E, ST-B, SS-A, and AmB were defined as the lowest concentrations at which scores of 0 were observed. The MIC for ketoconazole was described as the lowest concentrations at which a score of 2 was observed.

Example 7

Minimum Fungicidal Concentration (MFC): MFC values were determined by subculturing 10 $\mu$l from each well with a drug concentration higher than the MIC, equal to the MIC, and one well lower than the MIC on drug-free SDA when the MICs were read. Incubation temperatures were the same as the MICs. Incubation times were 24 hr for *Candida* spp., *S. cerevisiae,* and *Mucor* spp; 48 hr for *C. neoformans* and *A. fumigatus;* and 7 d for *Microsporum* and *Trichophyton* spp. The MFC was the lowest concentration with three or fewer colonies/plate for the yeasts and no growth for the filamentous fungi.

Example 8

Erythrocyte Toxicity: Sheep red blood cell (RBC) hemolysis was used to assess erythrocyte toxicity of the CLPs and AmB. RBCs (MicroBio Products, Inc., Salt Lake City, Utah) were washed four times with phosphate-buffered-saline (PBS) by centrifugation at 800× g for 10 min and adjusted to $1\times10^8$ cells/ml as previously described by Chavanet, P., V. Joly, D. Rigaud, J. Bolard, C. Carbon, and P. Yeni. 1994. Influence of diet on experimental toxicity of amphotericin B deoxycholate. *Antimicrob. Agents Chemother.* 38(5):963–968. RBCs and a 2× concentration of SR-E, ST-B or SS-A in PBS were mixed in a 1:1 ratio and incubated at 37° C. for 1 hr. After incubation, cells were pelleted by centrifugation at 800× g for 10 min and the supernatant was collected and the absorbance at 550 nm was determined. To verify that the compound did not affect the absorbance reading, the pellet was washed with PBS, lysed with distilled water, and the supernatant absorbance determined after centrifugation. Distilled water and PBS were used as lysis and hemoglobin retention controls, respectfully, as described by National Committee for Clinical Laboratory Standards. 1992. Reference method for broth dilution antifungal susceptibility testing of yeasts; proposed standard, NCCLS document M27-P (ISBN 1-56238-186-5). NCCLS, Villanova.

Example 9

Lipodepsipeptide for Immunosuppression Experiments: SR-E was purified as previously described in Bidwai, A. P., Bachmann, R. C. and Takemoto, J. Y., "Mechanism of action of Pseudomonas syringae phytotoxin syringomycin". Plant Physiol. 83:39–43 (1987). A stock solution (10 mg per ml) was prepared in RPMI1640 culture media, aliquoted and stored frozen at −20°. SR-E was thawed on ice, diluted appropriately and used fresh in lymphocyte cultures at the concentrated indicated in FIGS. 3 and 4.

Example 10

Lymphocyte stimulation: Lymphocyte stimulation was performed with three different mitogens: phytohemagglutinin (PHA), pokeweed mitogen (PWM), and monoclonal antibody to CD3 (anti-CD3). Using methods well known in the art, PHA and PWM (both from Sigma Chemical Co.) and anti-CD3 (AMAC, Inc.) were administered at final concentrations of 10 $\mu$g, 20$\mu$ and 0.4 $\mu$g per ml, respectively, on cultured lymphocytes.

Example 11

Mitogen-induced lymphocyte proliferation: Peripheral blood mononuclear cells (MNC) (containing lymphocytes and monocytes) were separated by Ficoll-Hypaque density-gradient centrifugation using techniques well known in the art. Mitogen-induced lymphocyte proliferation was determined as previously described in Singh, V. K., "Stimulatory effect of corticotropin-releasing neurohormone on human lymphocyte proliferation and interleukin-2 receptor expression". J.Neuroimmunol.23.257–262 (1989). Briefly, MNC were cultured in triplicate in 96-well microtiter plates (Corning, Inc.). The cultures (final volume of 200 $\mu$l) contained $10^5$ cells, various mitogens, and different concentrations of SR-E in RPMI1640 containing fetal bovine serum at a final concentration of 5% (V/V). The blank cultures did not contain mitogen or SR-E. Cultures were incubated for 4 days in a humidified chamber with 5% $CO_2$ at 37° C.

Example 12

[$^3$H]-thymadine Incorporation: Cells were pulse-labeled for 4 hours with 0.5 $\mu$Ci/well of [$^3$H]methyl-thymidine (spec. act.=25 Ci/mmol from Amersham Intl.). The cells were collected using a semi-automatic cell harvester (Skatron, Inc.) onto filter paper discs, air-dried and transferred to vials. To each vial, 2 ml of CytoScint fluid (ICN Biomedicals) was dispensed and the radioactivity determined using a liquid scintillation counter (Tri-Carb, Packard). The rate of [$^3$H]-thymidine incorporation by MNC was calculated as counts per minute per $10^{5}$ cells.

7. SUMMARY

In summary, strains of *Pseudomonas syringae* pv. *syringae* produce CLPs with antifungal activity. In vitro antifungal and fungicidal activities of three CLPs syringomycin E, syringotoxin B, and syringostatin A were evaluated using a standard broth microdilution susceptibility method against medically important isolates. Erythrocyte toxicity was also evaluated. All three compounds showed broad antifungal activity and fungicidal action against most of the fungi tested. Overall, the cyclic lipodepspeptides were more effective against yeasts than against the filamentous fungi. Syringomycin E and syringostatin A had very similar antifungal activity (2.5–>40 g/ml) and erythrocyte toxicity. Syringotoxin B was generally less active (0.8–200 g/ml) than syringomycin E and syringostatin A against most fungi and less toxic to erythrocytes.

In addition, CLPs displayed significant immunosuppressive activity. One CLP, syringomycin-E, had no effect on [$^3$H]-thymadine incorporation in the absence of mitogens. However, syringomycin-E significantly inhibited [$^3$H]-thymadine incorporation in mitogen-induced lymphocyte. Syringomycin-E's suppressive effect was more pronounced with pokeweed mitogen (PWM) as compared to phytohemagglutinin (PHA) or monoclonal antibody to CD3 (anti-CD3). Given the mechanism of action of these mitogens, syringomycin-E suppresses both cellular and humoral immune responses.

What is claimed and desired to be secured by United States Letters Patent is:

1. A method for combating plant and mammalian pathogenic fungi comprising contacting the fungi with a cyclic lipodepsipeptide said lipodepsipeptide selected from the group consisting of syringomycin, syringostatin and syringotoxin.

2. The method for combating pathogenic fungi of claim 1 wherein the lipodepsipeptide is isolated from a plant bacterium *Psuedomonas stringae* pv. *syringae.*

3. The method for combating pathogenic fungi of claim 1 wherein the lipodepsipeptide is syringomycin-E.

4. The method for combating pathogenic fungi of claim 1 wherein the lipodepsipeptide is syringostatin-B.

5. The method for combating pathogenic fungi of claim 1 wherein the lipodepsipeptide is syringostatin-A.

6. A method for combating plant and mammalian pathogenic fungi comprising contacting the fungi with a compound comprising a lipodepsipeptide having a formula:

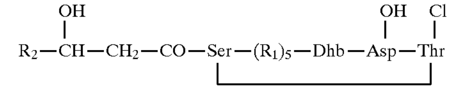

wherein $R_1$ is an amino acid or a modified amino acid; and $R_2$ is $H_3C-(CH_2)_n-$, wherein n is an even integer from 6–12.

7. The method for combating pathogenic pathogens of claim 6 wherein $R_1$ is selected from the group consisting of Ser-Dab-Dab-Arg-Phe, Dab-Dab-HomoSer-Orn-Thr and Dab-Gly-Homoser-Orn-Thr.

8. The method for combating pathogenic pathogens of claim 6 wherein $R_2$ is $CH_3(CH_2)_9$—CH(OH).

9. A method for combating pathogenic pathogens of claim 6 wherein R1 is Dab-Gly-HomoSer-Orn-Thr.

10. A method for combating pathogenic pathogens of claim 6 wherein R1 is Ser-Dab-Dab-Arg-Phe.

11. A method for combating pathogenic pathogens of claim 8 wherein R1 is Dab-Dab-HomoSer-Orn-Thr.

* * * * *